US009383564B2

(12) United States Patent
Fujita et al.

(10) Patent No.: US 9,383,564 B2
(45) Date of Patent: Jul. 5, 2016

(54) FLUORESCENCE OBSERVATION METHOD AND FLUORESCENCE OBSERVATION APPARATUS

(71) Applicant: OLYMPUS CORPORATION, Tokyo (JP)

(72) Inventors: Katsumasa Fujita, Tokyo (JP); Takeharu Nagai, Tokyo (JP); Kenta Saito, Tokyo (JP); Masahito Yamanaka, Tokyo (JP); Shinichi Takimoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/495,241

(22) Filed: Sep. 24, 2014

(65) Prior Publication Data

US 2015/0008340 A1    Jan. 8, 2015

Related U.S. Application Data

(63) Continuation of application No. PCT/JP2013/060255, filed on Mar. 25, 2013.

(30) Foreign Application Priority Data

Mar. 26, 2012    (JP) ................................. 2012-068686

(51) Int. Cl.
*G01T 1/20*    (2006.01)
*G02B 21/00*    (2006.01)
(Continued)

(52) U.S. Cl.
CPC ............ *G02B 21/0076* (2013.01); *A61B 6/037* (2013.01); *A61B 6/0478* (2013.01);
(Continued)

(58) Field of Classification Search
CPC ...... G01N 33/569; A61B 5/00; A61B 5/0059; A61B 5/0071
USPC ........................................................ 250/459.1
See application file for complete search history.

(56) References Cited

U.S. PATENT DOCUMENTS

| 5,523,573 A * | 6/1996 | Hanninen | G01N 21/6408 |
| | | | 250/459.1 |
| 2011/0044910 A1* | 2/2011 | Lin | G01N 33/56972 |
| | | | 424/9.6 |

FOREIGN PATENT DOCUMENTS

JP    2011-185844 A    9/2011

OTHER PUBLICATIONS

Xu et al. "Multiphoton fluorescence excitation: New spectral windows for biological nonlinear microscopy", PNAS, vol. 93, pp. 10763-10768, Oct. 1996.*

(Continued)

*Primary Examiner* — David Porta
*Assistant Examiner* — Meenakshi Sahu
(74) *Attorney, Agent, or Firm* — Scully, Scott, Murphy & Presser, P.C.

(57) ABSTRACT

A fluorescence observation method of the present invention for detecting plural types of fluorescence emitted from two or more kinds of fluorescent molecules includes: subjecting each of the two or more kinds of fluorescent molecules to multi-photon excitation by exciting light having an exciting wavelength equal to or shorter than 700 nm in a visible region, to generate fluorescence upon making use of an absorption wavelength band in a deep ultraviolet region of each of the two or more kinds of fluorescent molecules; and simultaneously detecting plural types of fluorescence generated on a shorter-wavelength side or on both of the shorter-wavelength side and a longer-wavelength side of the exciting wavelength of the exciting light.

11 Claims, 11 Drawing Sheets

(51) Int. Cl.
*A61B 6/03* (2006.01)
*A61B 6/00* (2006.01)
*A61B 6/04* (2006.01)
*G01T 1/29* (2006.01)
*G01N 21/64* (2006.01)

(52) U.S. Cl.
CPC ........... *A61B 6/501* (2013.01); *G01N 21/6458* (2013.01); *G01T 1/2985* (2013.01); *G01N 2021/6421* (2013.01); *G01N 2021/6471* (2013.01); *G01N 2201/068* (2013.01); *G01N 2201/0697* (2013.01)

(56) References Cited

OTHER PUBLICATIONS

International Search Report dated Jul. 12, 2013 issued in PCT/JP2013/060255.

Sun, Yun-Xu et al., "Study on multi-photon excited fluorescence combined with capillary electrophoresis", Database Medline [Online], US National Library of Medicine, Bethesda, MD (Apr. 2005) (Abstract).

Sun, Yun-Xu et al., "Study on multi-photon excited fluorescence combined with capillary electrophoresis", Guang Pu Xue Yu Guang Pu Fen Xi=Guang Pu (Apr. 2005), vol. 25, No. 4, pp. 502-505, with English Abstract.

Denk, Winfried et al., "Two-Photon Laser Scanning Fluorescence Microscopy", Science (Apr. 6, 1990), vol. 248, No. 4951, pp. 73-76.

Bi, Yan-Hua et al., "Two-photon-excited fluorescence and two-photon spectrofluoroelectrochemistry of riboflavin", Electrochemistry Communications (Apr. 1, 2006), vol. 8, No. 4, pp. 595-599.

Wise, Dana D. et al., "Quantitation of nicotinamide and serotonin derivatives and detection of flavins in neuronal extracts using capillary electrophoresis with multiphoton-excited fluorescence", Journal of Chromatography (Apr. 14, 2006), vol. 1111, No. 2, pp. 153-158.

Barry, N.P. et al., "Applications of Ultrafast Lasers to Two-Photon Fluroescence and Lifetime Imaging", Proceedings of SPIE (Jan. 23, 2002), vol. 4633, No. 23, pp. 50-61.

Stepanenko, Olesia V., "Comparative Studies on the Structure and Stability of Fluorescent Proteins EGFP, zFP506, mRFP1, "dimer2", and DsRed1", Biochemistry (2004), vol. 43, No. 47, pp. 14913-14923.

Gorokhovatsky, A.Y. et al., "Fusion of Aequorea victoria GFP and aequorin provides their Ca2+—induced interaction that results in red shift of GFP absorption and efficient bioluminescence energy transfer", Biochemical and Biophysical Research Communications, Jun. 19, 2004, vol. 320, pp. 703-711.

Japanese Office Action dated Mar. 8, 2016 from Japanese Patent Application No. 2012-068686, together with an English language translation.

* cited by examiner

FIG.11A
FIG.11B
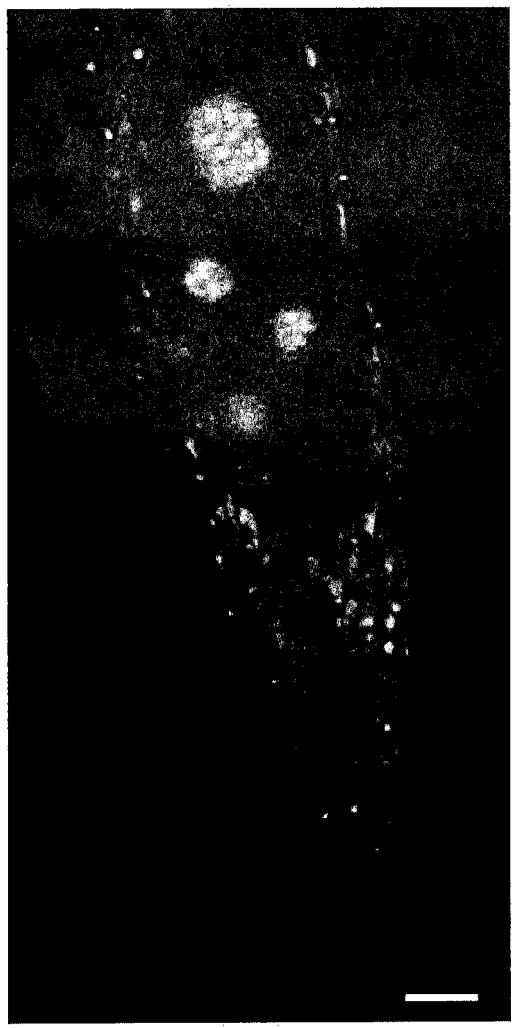

FLUORESCENCE OBSERVATION METHOD AND FLUORESCENCE OBSERVATION APPARATUS

This application is a continuation of PCT International Application No. PCT/JP2013/060255, filed on Mar. 25, 2013, and claims the benefit of Japanese Patent Application No. 2012-068686 filed in Japan on Mar. 26, 2012. The contents of PCT International Application No. PCT/JP2013/060255 and Japanese Patent Application No. 2012-068686 are incorporated herein by reference.

BACKGROUND OF THE INVENTION

1. Field of Invention

This invention relates to a fluorescence observation method of observing fluorescence emitted from fluorescent molecules like plural kinds of fluorescent proteins for example and relates to a florescence observation apparatus.

2. Description of Related Art

Observations of biomolecules using fluorescent molecules are standard methods of observation in the field of medicine or life science. Various fluorescent molecules which are different in fluorescence wavelength have been developed, and it becomes possible to observe plural kinds of biomolecules by using these fluorescent molecules in combination with one another.

In conventional methods of observing fluorescence emitted by a fluorescent molecule, for example, there exist: a method in which a fluorescent molecule is excited through one-photon excitation with light in the visible region and fluorescence generated on the longer-wavelength side of the wavelength of exciting light (Stokes shift) is detected; and a method in which a fluorescent molecule is excited through multi-photon excitation with light in the near-infrared region and fluorescence generated on the shorter-wavelength side of the wavelength of exciting light is detected (refer to Non Patent Literature 1, for example).

On the other hand, a method of exciting fluorescent proteins through one-photon excitation with light in the deep ultraviolet region is disclosed in the following Non Patent Literature 2. Non Patent Literature 2 discloses that fluorescent molecules (proteins) have absorption wavelength bands in the deep ultraviolet region and these fluorescent molecules have a common absorption wavelength band in the deep ultraviolet region even though these fluorescent molecules are different from one another.

As a result, if the fluorescent molecules are excited through one-photon excitation with light in the deep ultraviolet region and fluorescence generated on the longer-wavelength side of the wavelength of exciting light (Stokes shift) are detected, then it becomes possible to observe plural types of fluorescence simultaneously.

PRIOR ART LITERATURE LIST

Non Patent Literature

Non Patent Literature 1:
Science-1990, vol. 248, Winfried Denk et al., "Two-Photon Laser Scanning Fluorescence Microscopy", Science, New Series, Vol. 248, No. 4951 (Apr. 6, 1990), pp. 73-76
Non Patent Literature 2:
Biochemistry. 2004 Nov. 30, 43, 14913-14923, Turoverov et al., "Comparative studies on the structure and stability of fluorescent proteins EGFP, zFP506, mRFP1, "dimer2" and DsRed1"

The objective of the present invention is to offer: a fluorescence observation method and a fluorescence observation apparatus that make it possible to simultaneously observe plural types of fluorescence emitted from plural kinds of fluorescent molecules with a simple optical configuration as dispensing with plural kinds of exciting wavelengths, while causing little damage to an observed object for which the fluorescent molecules are used as fluorescent labels and allowing use of common glass as an optical material for the fluorescence observation.

SUMMARY OF INVENTION

In order to achieve the above objective, a fluorescence observation method for detecting plural types of fluorescence emitted from at least two or more kinds of fluorescent molecules according to the present invention is characterized in that the fluorescence observation method includes: subjecting each of the two or more kinds of fluorescent molecules to multi-photon excitation by exciting light having an exciting wavelength equal to or shorter than 700 nm in a visible region, to generate fluorescence upon making use of an absorption wavelength band in a deep ultraviolet region of each of the two or more kinds of fluorescent molecules; and simultaneously detecting plural types of fluorescence generated on a shorter-wavelength side or on both of the shorter-wavelength side and a longer-wavelength side of the exciting wavelength of the exciting light.

Also, in a fluorescence observation method of the present invention, it is preferred that each of the two or more kinds of fluorescent molecules used for a fluorescence detection target has absorption wavelength bands in the deep ultraviolet region and in the visible region.

Also, in a fluorescence observation method of the present invention, it is preferred that the exciting light is an ultrashort-pulsed laser beam.

Also, in a fluorescence observation method of the present invention, it is preferred that only fluorescence generated on the shorter-wavelength side of the exciting wavelength is detected via a short-pass filter.

Also, in a fluorescence observation method of the present invention, it is preferred that fluorescence having a wavelength of 400 nm or longer generated on the shorter wavelength side of the exciting wavelength is detected.

Also, in a fluorescence observation method of the present invention, it is preferred that the plural types of fluorescence generated via the multi-photon excitation are detected in a spectrally-selective manner.

Also, in a fluorescence observation method of the present invention, it is preferred that the plural types of fluorescence generated via the multi-photon excitation are detected through confocal detection.

Also, in a fluorescence observation method of the present invention, it is preferred that fluorescence deriving from one photon and fluorescence deriving from two photons, which are generated via the multi-photon excitation, are simultaneously detected.

Also, a fluorescence observation apparatus according to the present invention is characterized in that the fluorescence observation apparatus includes: a light source that emits, at a high density, light having a predetermined wavelength; a second-harmonic generating element that generates second harmonic waves having a wavelength of 700 nm or shorter in a visible region, using the light from the light source; and a microscope configured to subject plural kinds of fluorescent molecules to multi-photon excitation by the light generated by the second-harmonic generating element, so that plural types of fluorescence generated on a shorter-wavelength side or on both of the shorter-wavelength side and a longer-wavelength side of the wavelength of the exciting light by the fluorescent molecules are simultaneously observable.

Also, a fluorescence observation apparatus according to the present invention is characterized in that the fluorescence observation apparatus includes an exciting light generating unit integrally provided with the light source unit and the second harmonic generating element, so as to subject the plural kinds of the fluorescent molecules to multi photon-excitation by the light generated by the exciting light generating unit.

Also, in a fluorescence observation apparatus of the present invention, it is preferred that the second-harmonic generating element is configured to be insertable in and removable from a path of light from the light source.

According to the present invention, it is possible to obtain a fluorescence observation method and a fluorescence observation apparatus that make it possible to simultaneously observe plural types of fluorescence emitted from plural kinds of fluorescent molecules with a simple optical configuration as dispensing with plural kinds of exciting wavelengths, while causing little damage to an observed object for which the fluorescent molecules are used as fluorescent labels and allowing use of common glass as an optical material for the fluorescence observation.

These and other features and advantages of the present invention will become apparent from the following detailed description of the preferred embodiments when taken in conjunction with the accompanying drawings.

BRIEF DESCRIPTION OF DRAWINGS

FIG. 6A is a graph in the case where a fluorescent protein, Sirius, is used as a fluorescent molecule, FIG. 6B is a graph in the case where a fluorescent protein, mseCFP, is used as a fluorescent molecule, FIG. 6C is a graph in the case where a fluorescent protein, mTFP1, is used as a fluorescent molecule, and FIG. 6D is a graph in the case where a fluorescent protein, EGFP, is used as a fluorescent molecule.

FIG. 7A is a diagram showing one example of them, FIG. 7B is a diagram showing one example of variations of the example shown in FIG. 7A, and FIG. 7C is a diagram showing another example of variations of the example shown in FIG. 7A.

FIG. 10A is a photograph of a fluorescent image with the fluorescent protein, Sirius, FIG. 10B is a photograph of a fluorescent image with the fluorescent protein, mseCFP, FIG. 10C is a photograph of a fluorescent image with the fluorescent protein, mTFP1, and FIG. 10D is a photograph of a fluorescent image with the fluorescent protein, EGFP.

FIGS. 11A and 11B are images obtained by processing fluorescent signals detected by each of detectors with a fluorescence-wavelength separating (UNMIXING) method or the like in the fluorescent images of the HeLa cell in which the four fluorescent proteins are expressed with the fluorescence observation method of the embodiment 1, removing bleed-through of fluorescence components other than the fluorescence mainly detected by each of the detectors, and then superposing the fluorescent images having been processed: FIG. 11A is a fluorescent image of the cell on a X-Y plane; and FIG. 11B is a fluorescent image of the cell on a X-Z plane.

DETAILED DESCRIPTION OF THE PREFERRED EMBODIMENT

Prior to the explanation of embodiments of the present invention, operation effects of the present invention are explained.

A fluorescence observation method for detecting plural types of fluorescence emitted from at least two or more kinds of fluorescent molecules according to the present invention includes: subjecting each of the two or more kinds of fluorescent molecules to multi-photon excitation by exciting light having an exciting wavelength equal to or shorter than 700 nm in a visible region, to generate fluorescence upon making use of an absorption wavelength band in a deep ultraviolet region of each of the two or more kinds of fluorescent molecules; and simultaneously detecting plural types of fluorescence generated on a shorter-wavelength side or on both of the shorter-wavelength side and a longer-wavelength side of the exciting wavelength of the exciting light.

The course of events that lead to the achievement of fluorescence observation methods of the present invention is explained.

Figure 1:
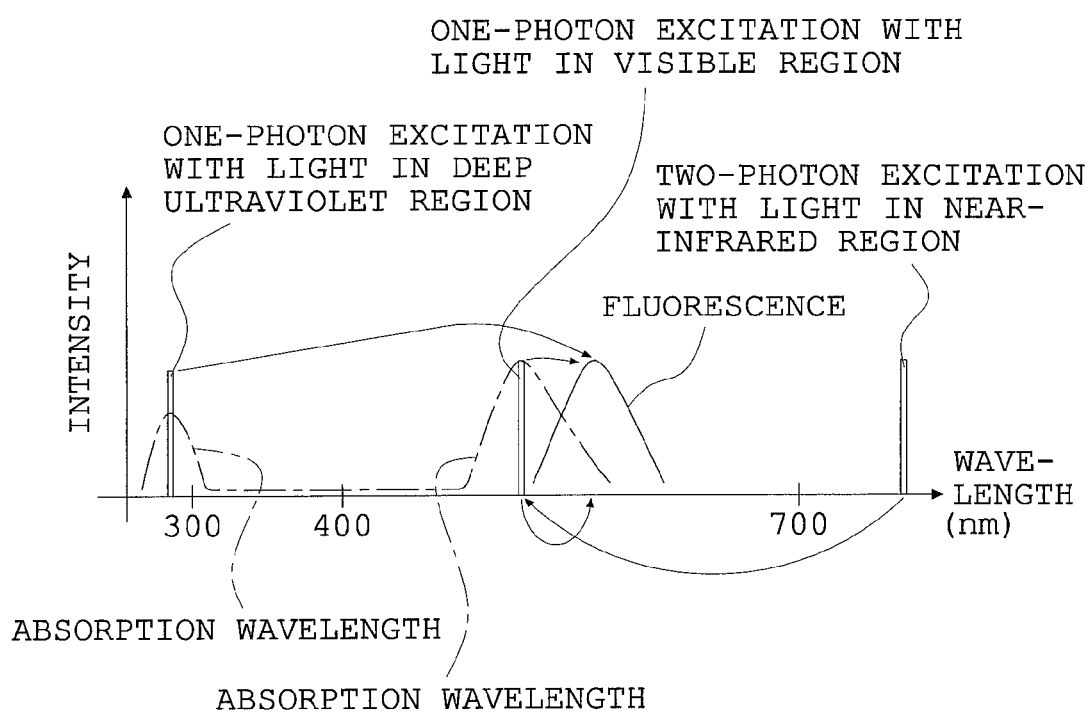
FIG. 1 is a graph conceptually showing the spectra of fluorescence generated by fluorescent molecules through one-photon excitation with light in the visible region, through two-photon excitation with light in the near-infrared region, and through one-photon excitation with light in the deep ultraviolet region, respectively, in the prior art.
Figure 2:
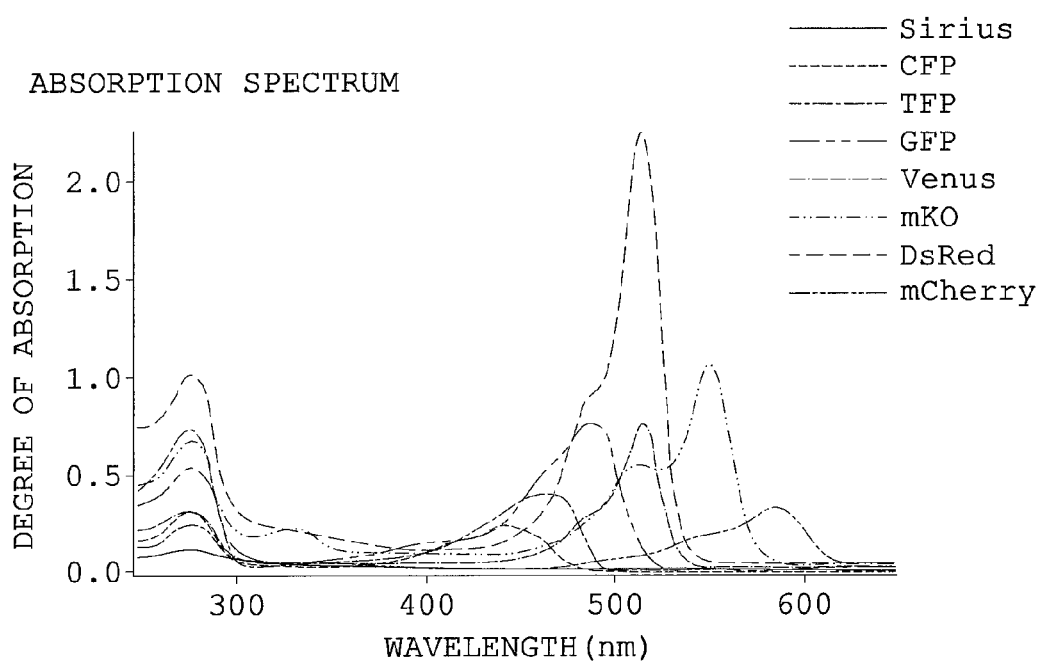
FIG. 2 is a graph showing absorption spectra of plural kinds of fluorescent proteins.
Figure 3:
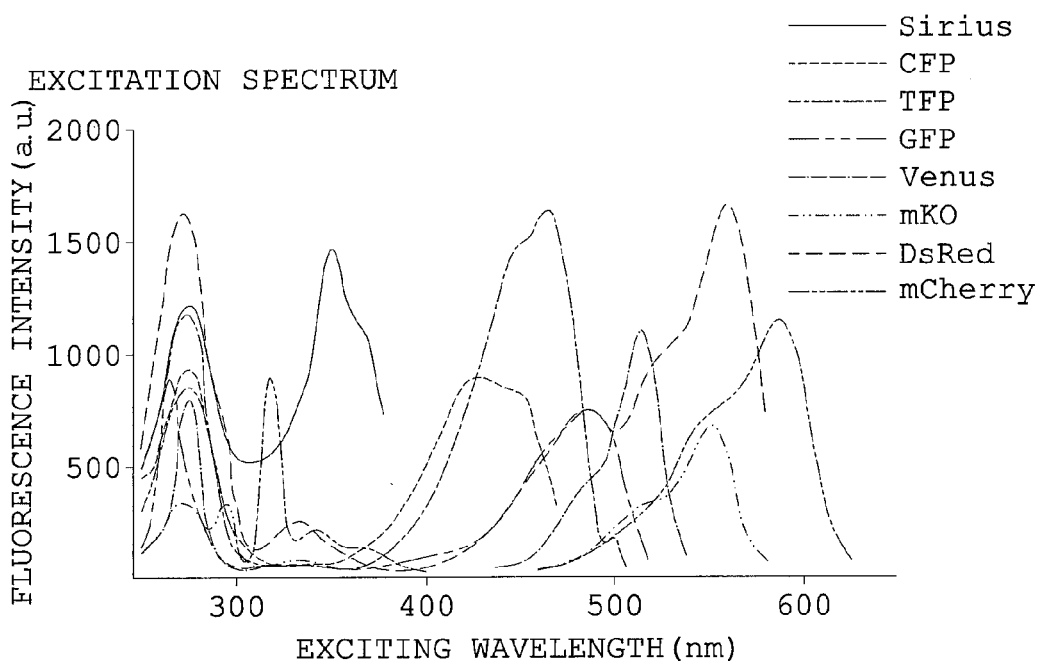
FIG. 3 is a graph showing excitation spectra of the fluorescent proteins shown in FIG. 2.
Figure 4:
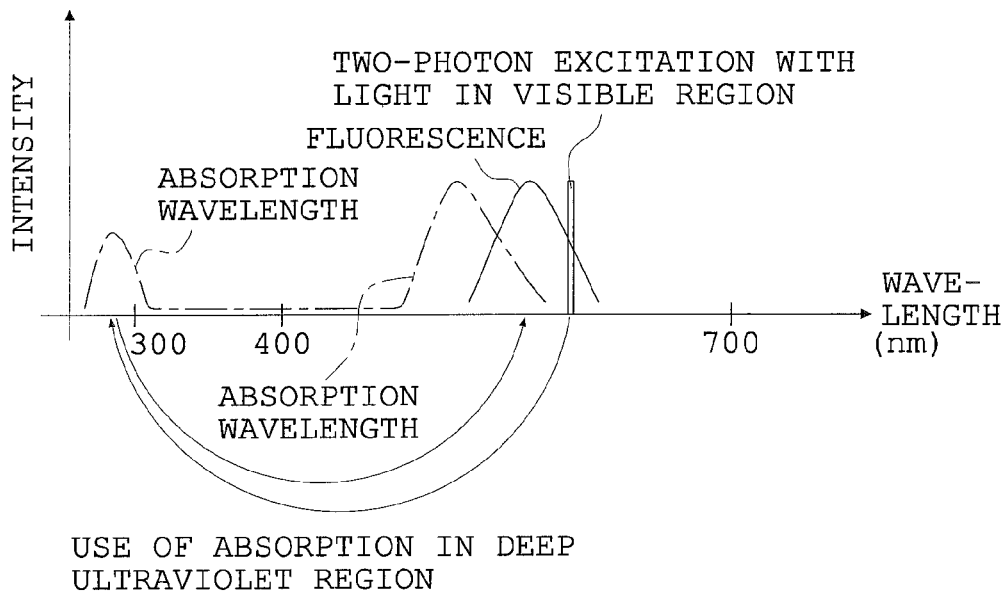
FIG. 4 is a graph conceptually showing a spectrum of fluorescence generated from one fluorescent molecule, in multi-photon excitation with light in the visible region according to a fluorescence observation method of the present invention.
Figure 5:
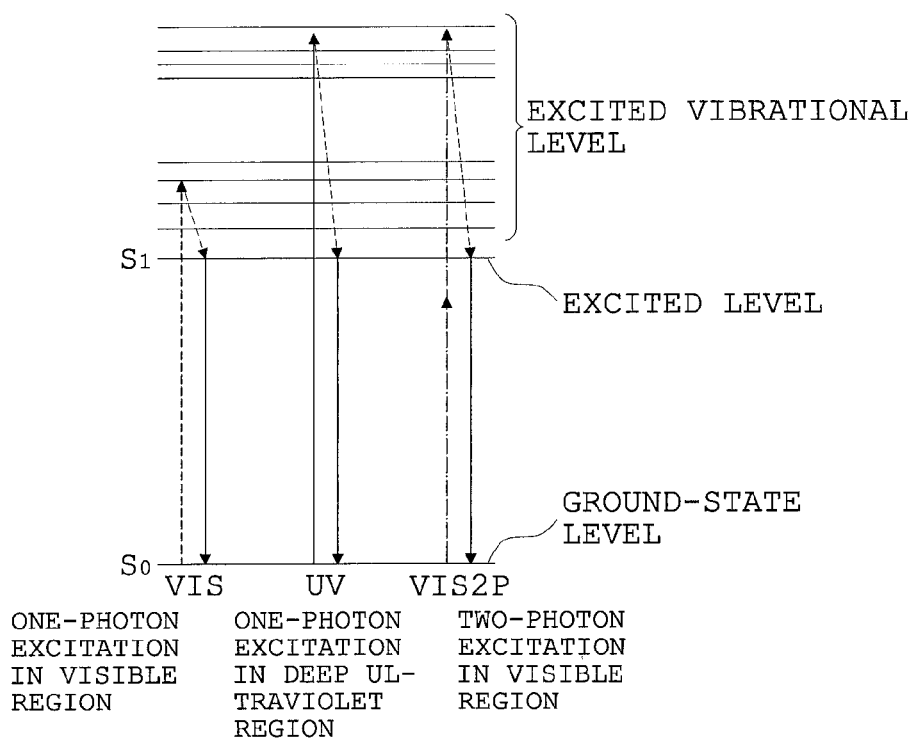
FIG. 5 is an explanatory view showing energy states: in one-photon excitation with light in the visible region and in one-photon excitation with light in the deep ultraviolet region in the prior art; and in multi-photon excitation with light in the visible region according to a fluorescence observation method of the present invention, respectively.
Figure 6A:
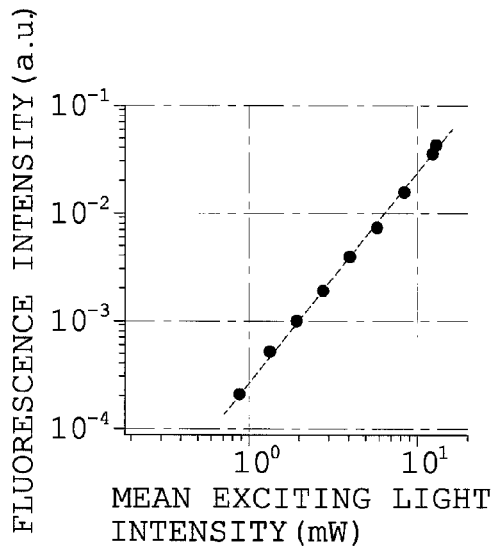
FIGS. 6A to 6D are views showing the relation between exciting light intensity and acquired fluorescence intensity in two-photon excitation in the case where different fluorescent molecules are used separately from one another.
Figure 6B:
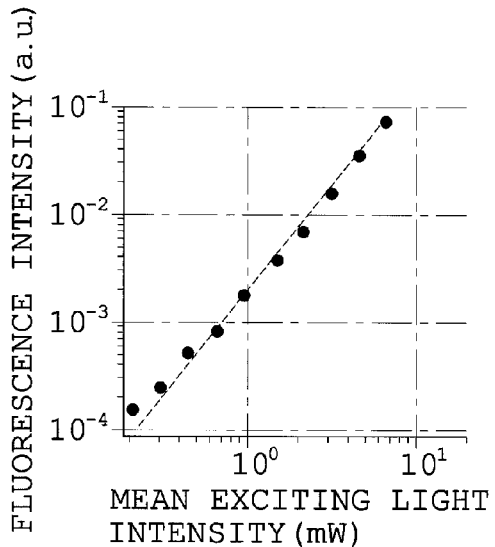
Figure 6C:
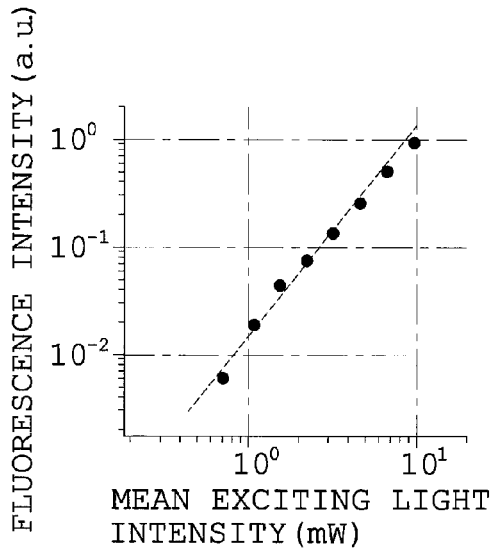
Figure 6D:
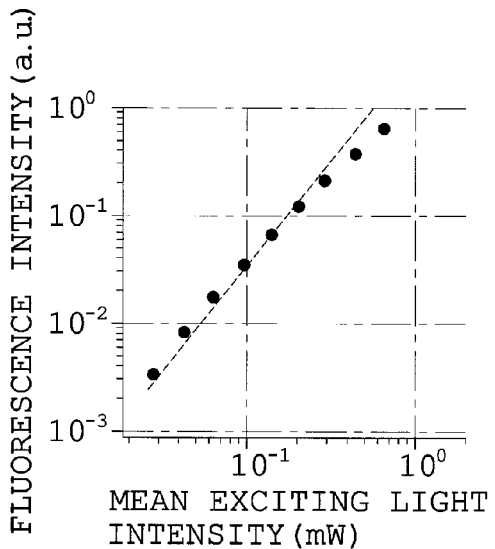

FIG. 1 is a graph conceptually showing the spectra of fluorescence generated by fluorescent molecules through one-photon excitation with light in the visible region, through two-photon excitation with light in the near-infrared region, and through one-photon excitation with light in the deep ultraviolet region, respectively, in the prior art. FIG. 2 is a graph showing absorption spectra of plural kinds of fluorescent proteins. FIG. 3 is a graph showing excitation spectra of the fluorescent proteins shown in FIG. 2. FIG. 4 is a graph conceptually showing a spectrum of fluorescence generated from one fluorescent molecule in multi-photon excitation with light in the visible region according to a fluorescence observation method of the present invention. FIG. 5 is an explanatory view showing energy states in one-photon excitation with light in the visible region and in one-photon excitation with light in the deep ultraviolet region in the prior art and in multi-photon excitation with light in the visible region according to a fluorescence observation method of the present invention respectively. FIGS. 6A to 6D are a view showing the relation between exciting light intensity and acquired fluorescence intensity in two-photon excitation in the case where different fluorescent molecules are used separately from one another; FIG. 6A is a graph in the case where a fluorescent protein, Sirius, is used as a fluorescent molecule, FIG. 6B is a graph in the case where a fluorescent protein, mseCFP, is used as a fluorescent molecule, FIG. 6C is a graph in the case where a fluorescent protein, mTFP1, is used as a fluorescent molecule, and FIG. 6D is a graph in the case where a fluorescent protein, EGFP, is used as a fluorescent molecule.

As shown in FIG. 1, when a fluorescent molecule is excited through one-photon excitation with light in the visible region, fluorescence having wavelengths longer than the wavelength of exciting light is generated. Also, when a fluorescent molecule is excited through two-photon excitation with light in the near-infrared region, fluorescence having wavelengths shorter than the wavelength of the exciting light is generated. Also, when a fluorescent molecule is excited through one-photon excitation with light in the deep ultraviolet region, fluorescence having wavelengths longer than the wavelength of the exciting light is generated.

Also, as shown in FIG. 2, fluorescent proteins have absorption wavelength bands in the visible region and in the deep ultraviolet region. The absorption wavelength bands in the visible region are used as absorption wavelength bands for exciting the fluorescent proteins in one-photon excitation with light in the visible region and in two-photon excitation with light in the near-infrared region, these excitations being usually performed.

Also, as shown in FIG. 2, many fluorescent molecules have a common absorption wavelength band in the deep ultraviolet region.

The excitation spectra shown in FIG. 3 are obtained by graphing a result of measurement of the intensity of fluorescence emitted by each of the fluorescent proteins, the measurement being preformed while a change of excitation wavelength is being made. Efficiencies in excitation at respective exciting wavelengths can be compared with one another with these excitation spectra. It can be understood that efficiencies in excitation which are comparable with those in the visible region can be obtained also in the deep ultraviolet region by the graph shown in FIG. 3.

Now, it is known that fluorescence is generated when: an electron makes a transition from the ground-state level to an excited level as a result of absorption of a photon of exciting light having a predetermined wavelength into a fluorescent molecule; and then the electron makes a transition to the ground-state level via thermal vibrational relaxation. Also, methods for generating fluorescence can be roughly classified into "one-photon absorption fluorescence" and "two-photon (multi-photon) absorption fluorescence" in accordance with differences in excitation process. In one-photon absorption fluorescence, one photon of exciting light is absorbed by a fluorescent molecule, so that an electron in the fluorescent molecule makes a transition to an excited level. On the other hand, in two-photon absorption fluorescence, two photons of exciting light are simultaneously absorbed by a fluorescent molecule, so that an electron in the fluorescent molecule makes a transition to an excited level. Also, in one-photon absorption fluorescence, light having approximately the same energy (wavelength) as the energy difference between the ground-state level and the excited level in a fluorescent molecule has to be used as exciting light. On the other hand, in two-photon absorption fluorescence, light having energy (wavelength) smaller than the energy difference can be used as exciting light. In general, in the case where the same kinds of fluorescent molecules are excited, the wavelength of exciting light for two-photon absorption fluorescence is longer than that for one-photon absorption fluorescence. Also, it is known that the intensity of fluorescence generated through the process of two-photon absorption is proportional to the square of the intensity of the exciting light (square property).

Accordingly, as shown in FIG. 4, the present inventors conceived the idea of generating fluorescence via a multi-photon absorption process using absorption by a fluorescent molecule in the deep ultraviolet region and the idea of using light in the visible region as exciting light. Fluorescent proteins have absorption properties characterized in that their efficiencies in excitation are good in the deep ultraviolet region. In the case where the fluorescent proteins are excited through two-photon excitation by using light having a wavelength longer than the absorption wavelength as exciting light, for example, by using a photon having a wavelength of 525 nm in the visible region, the fluorescent proteins efficiently generate two-photon absorption fluorescence on the basis of absorption by each of these fluorescent proteins in the deep ultraviolet region (FIG. 5). Also, as described above, the intensity of fluorescence generated through the two-photon absorption is proportional to the square of the intensity of exciting light.

Accordingly, use of two-photon absorption fluorescence makes it possible to obtain fluorescence comparable to fluorescence that is generated via excitation with light in the deep ultraviolet region (one-photon absorption fluorescence), while using light in the visible region as exciting light.

In order to demonstrate that fluorescence can be generated by exciting a fluorescent molecule through multi-photon excitation with light in the visible region, the present inventors tried two-photon excitation for plural kinds of fluorescent proteins using light having a visible wavelength.

FIGS. 6A to 6D are views showing the relation between exciting light intensity and acquired fluorescence intensity (each intensity is plotted logarithmically) in two-photon excitation in the case where different fluorescent molecules are used separately from one another; FIG. 6A is a graph in the case where a fluorescent protein, Sirius, is used as a fluorescent molecule, FIG. 6B is a graph in the case where a fluorescent protein, mseCFP, is used as a fluorescent molecule, FIG. 6C is a graph in the case where a fluorescent protein, mTFP1, is used as a fluorescent molecule, and FIG. 6D is a graph in the case where a fluorescent protein, EGFP, is used as a fluorescent molecule. The wavelength of exciting light is 525 nm.

As shown in each of the graphs in FIGS. 6A, 6B, 6C and 6D, whichever of the fluorescent proteins is used as a fluorescent molecule, the intensity of fluorescence is proportional to the square of the intensity of the exciting light (the slope of the approximated straight line of each logarithmic plot is about 2). This shows that the detected fluorescence is generated by two-photon excitation.

The present inventors conceived a fluorescence observation method for detecting plural types of fluorescence emitted from at least two or more kinds of fluorescent molecules through such a consideration and such a demonstration, the fluorescence observation method including: subjecting each of the two or more kinds of fluorescent molecules to multi-photon excitation by exciting light having an exciting wavelength equal to or shorter than 700 nm in a visible region, to generate fluorescence upon making use of an absorption wavelength band in a deep ultraviolet region of each of the two or more kinds of fluorescent molecules; and simultaneously detecting plural types of fluorescence generated on a shorter-wavelength side or on both of the shorter-wavelength side and a longer-wavelength side of the exciting wavelength of the exciting light.

As in the fluorescence observation method of the present invention, use of light with a wavelength of 700 nm or shorter in the visible region as exciting light for multi-photon excitation of fluorescent molecules can dispense with plural kinds of exciting wavelengths in detecting fluorescence emitted from at least two or more kinds of the fluorescent molecules. As a result, an optical system or the like for merging exciting light in the same path, which is necessary for use of plural types of exciting light different from one another in wavelength, can be dispensed with, to avoid complicated configuration of the optical system. Also, as described above, while application of plural types of exciting light different from one another in wavelength to fluorescence observation would break spatial coincidence because the exciting light, which is to be collected on a specimen surface, has focal positions varying with wavelength due to chromatic aberration, the fluorescence observation method of the present invention can dispense with use of plural types of exciting light and thus there is no need to take chromatic aberration on the specimen surface into consideration. In addition, the fluorescence observation method of the present invention does not require that, for performing fluorescence observation, plural types of exciting light different in wavelength are alternated for each fluorescent molecule, and thus is advantageous to simultaneous observation of movement of plural kinds of biomolecules.

Also, light having a wavelength of 700 nm or shorter in a visible region, which is used as exciting light in the fluorescence observation method of the present invention, has photon energy that is smaller than that of light in the deep ultraviolet region. Also, multi-photon excitation is utilized in the method of the present invention, so that light in the deep ultraviolet region is not absorbed by fluorescent molecules through areas of the fluorescent molecules except an area including a focal point. As a result, the fluorescence observation method according to the present invention makes it possible to reduce photo-damage to a specimen which is labeled with fluorescent molecules.

Also, light in the visible region is used as exciting light in a fluorescence observation method according to the present invention, so that commonly used glass or the like can be used as an optical material used for optical systems.

The probability of occurrence of multi-photon absorption is proportional to the squares of photon density (square property). Accordingly, multi-photon excitation is used in the fluorescence observation method of the present invention, so that the volume of portions in which fluorescent molecules are excited can be reduced to be remarkably smaller than that of portions at the focal position of the exciting light. It is possible to detect fluorescence with a resolution that is higher than resolutions determined in accordance with the wavelength of exciting light in one-photon excitation. As a result, just as a resolution in one-photon excitation with the visible region can be obtained in multi-photon excitation with the near-infrared region, so a resolution which is comparable to a resolution obtained in one-photon excitation with the deep ultraviolet region can be obtained through multi-photon excitation with the visible region according to the fluorescence observation method according to the present invention.

In addition, light in the visible region is used as exciting light in the fluorescence observation method of the present invention, so that it is possible to make optical systems by using only members transmitting or reflecting light in the visible region and coating. As a result, transmittance and reflectance of light can be increased, so that it is possible to improve the performance of the optical systems.

Besides, in the fluorescence observation method of the present invention, each of fluorescent molecules used for a fluorescence detection target is a fluorescent molecule having absorption wavelength bands in the deep ultraviolet region and in the visible region. For this reason, when a fluorescent molecule having the property of having an absorption spectrum that overlaps with exciting light is excited through multi-photon excitation, fluorescence components deriving from multi-photon excitation and from one-photon excitation respectively can occur.

Also, in a fluorescence observation method of the present invention, it is preferred that an ultrashort-pulsed laser beam is used as exciting light. Such a manner makes it possible to increase a photon density spatially and temporally at a focal point, so that two-photon excitation can be efficiently carried out.

Also, the spectral shape of an ultrashort-pulsed laser beam may be shaped with wavelength-selecting means such as band-pass filters and edge filters. Such a manner makes it easy to separate fluorescence and exciting light from each other, and, also, it is possible to detect fluorescence emission more efficiently. For example, the spectrum of an ultrashort-pulsed laser beam having a wide spectral width may be cut out by using edge filters in combination with one another to have a rectangular shape. Such a manner makes it possible to widen a wavelength band available to detect fluorescence emission. The temporal shape of the ultrashort-pulsed laser is widened by cutting out its spectral shape and shaping the spectral shape into a rectangle, so that it becomes possible to detect fluorescence emission more efficiency, although the efficiency of two-photon excitation deteriorates somewhat.

Also, in a fluorescence observation method of the present invention, it is preferred that only fluorescence generated on the shorter-wavelength side of the exciting wavelength of exciting light is detected via a short-pass filter.

In the case where a fluorescent molecule having the property of having an absorption spectrum that overlaps with exciting light is excited through multi-photon excitation by light having a wavelength of 700 nm or shorter in the visible region, fluorescence components deriving from two-photon excitation and from one-photon excitation respectively occur, as described above. It is known that fluorescence generated by one-photon excitation usually has a wavelength longer than that of exciting light (Stokes shift). Accordingly, in the case where a fluorescent molecule is excited through multi-photon excitation with the fluorescence observation method of the present invention, a fluorescence component generated by one-photon excitation also is contained on the longer-wavelength side of the exciting wavelength of the exciting light. However, if fluorescence components generated by one-photon excitation, which has a wavelength longer than that of the exciting light, is removed by using a short-pass filter or the like and only fluorescence components having wavelengths shorter than that of the exciting light are detected in a spectrally-selective manner, then it is possible to efficiently detect fluorescence generated by two-photon excitation.

Also, in a fluorescence observation method of the present invention, it is preferred that fluorescence having a wavelength of 400 nm or longer generated on the shorter-wavelength side of the exciting wavelength of exciting light is detected.

Such a manner makes it possible to separate auto-fluorescence deriving from a living auto-fluorescence substance like DNA or amino acids constituting proteins from fluorescence deriving from the fluorescent molecule, so that a high-contrast fluorescent imaging can be performed.

Also, in a fluorescence observation method of the present invention, it is preferred that the plural types of fluorescence generated via multi-photon excitation are detected in a spectrally-selective manner.

In order to detect fluorescence in a spectrally-selective manner, for example, multi-channel detector, a plurality of photomultiplier tubes, and dichroic mirror may be used in combination with one another, or a multi-focus mechanism and an imaging sensor like CCD, CMOS, or the like may be used in combination with one another.

Besides, in the fluorescence observation method of the present invention, plural types of fluorescence which are different in wavelength are generated simultaneously. Accordingly, in the case where the wavelength bands of the plural types of fluorescence overlap with one another, fluorescence generated by fluorescent molecules except a particular fluorescent molecule also may be inevitably detected by a detector in detecting only a fluorescence signal generated by the particular fluorescent molecule by the detector (fluorescence cross-talk). In such a case, it is preferred that: fluorescence signals detected by the detector are processed through a fluorescence-wavelength separating (UNMIXING) method or the like; and then fluorescence components deriving from fluorescent molecules except the particular fluorescent molecule are removed.

Also, in a fluorescence observation method of the present invention, it is preferred that plural types of fluorescence generated via multi-photon excitation are detected through confocal detection.

In more detailed explanation, a pinhole, a slit, or the like may be placed in front of a detector for detecting fluorescence so that fluorescence is detected through confocal detection.

Such a manner makes it possible to remove fluorescence generated by one-photon excitation and occurring outside its detecting plane.

In addition, an optical sectioning effect (which is an effect of acquiring an image such as only a part on a contour line is cut out) is also improved.

Also, in a fluorescence observation method of the present invention, fluorescence deriving from one photon and fluorescence deriving from two photons, which are generated via the multi-photon excitation, may be simultaneously detected. Such a manner makes it possible to increase the number of kinds of fluorescence which can be detected simultaneously through excitation.

Also, a fluorescence observation apparatus according to the present invention includes: a light source that emits, at a high density, light having a predetermined wavelength; a second-harmonic generating element that generates second harmonic waves having a wavelength of 700 nm or shorter in a visible region, using the light from the light source; and a microscope configured to subject plural kinds of fluorescent molecules to excitation by the light generated by the second-harmonic generating element, so that plural types of fluorescence generated on a shorter-wavelength side or on both of the shorter-wavelength side and a longer-wavelength side of the wavelength of the exciting light by the fluorescent molecules are simultaneously observable.

Figure 7A:
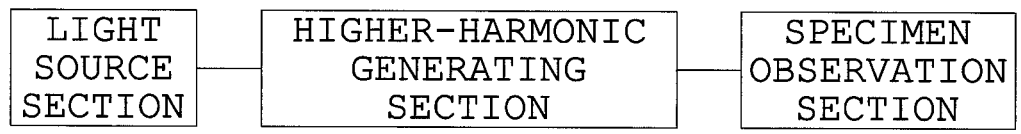
FIGS. 7A to 7C are block diagrams schematically showing the configurations of one mode for embodying the fluorescence observation apparatus according to the present invention.
Figure 7B:
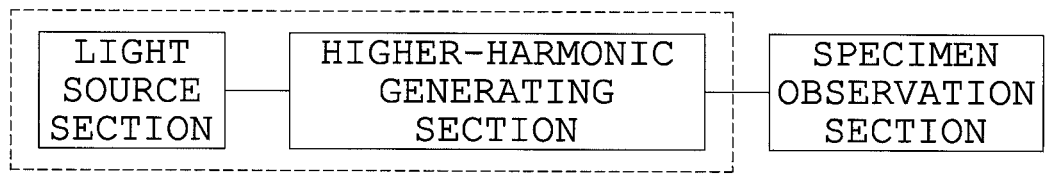
Figure 7C:
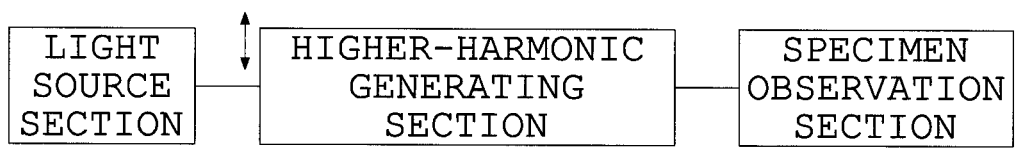

FIGS. 7A to 7C are block diagrams schematically showing structures of one embodiment of a fluorescence observation apparatus according to the present invention, FIG. 7A is a diagram showing one example of them, FIG. 7B is a diagram showing one example of variations of the example shown in FIG. 7A, and FIG. 7C is a diagram showing another example of variations of the example shown in FIG. 7A.

A fluorescence observation apparatus of the example shown in FIG. 7A includes a light source unit, a second-harmonic generating unit, and a unit for specimen observation.

The light source unit is composed of a light source that emits, at a high density, a laser-pulse beam having a predetermined wavelength, the light source being mode-locked laser, variable wavelength laser, OPO (optical Parametric Oscillator), or the like, for example.

The second-harmonic generating unit includes a SGH (Second harmonic generation) crystal like LBO (LiB3O5: Lithium triborate) crystal or BBO (Barium Borate) crystal, and the second-harmonic generating unit is composed of an element generating second harmonic waves having a wavelength of 700 nm or shorter in the visible region using light from the light source unit.

The unit for specimen observation is composed of a microscope configured to subject plural kinds of fluorescent molecules to multi-photon excitation by the light generated by the second-harmonic generating unit, so that plural types of fluorescence generated on the shorter-wavelength side or on both of the shorter-wavelength side and the longer-wavelength side of the wavelength of the exciting light by the fluorescent molecules are simultaneously observable, the microscope being laser scanning microscope, multi-photon fluorescence microscope, confocal fluorescence microscope, or the like, for example.

Such a constitution makes it possible to perform fluorescence observation using a fluorescence observation method of the present invention.

Besides, as shown in FIG. 7B, a fluorescence observation apparatus according to the present invention may be configured to include: an exciting light generating unit integrally provided with the light source unit and the second-harmonic generating element; and a microscope configured to subject plural kinds of fluorescent molecules to multi-photon excitation by the light generated by the exciting light generating unit, so that plural types of fluorescence generated on a shorter-wavelength side or on both of the shorter-wavelength side and a longer-wavelength side of the wavelength of the exciting light by the fluorescent molecules are simultaneously observable. The fluorescence observation apparatus formed in such a manner does not require an optical system for connecting the light source unit and the second-harmonic generating unit outside, so that it is possible to simplify the structure of the apparatus.

Alternatively, in a fluorescence observation apparatus of the present invention, as shown in FIG. 7C, the second-harmonic generating element may be configured to be insertable in and removable from a path of light from the light source.

Such a manner makes it possible to realize plural kinds of observation methods with one endoscope. For example, in combination with a multi-photon endoscope, it is possible to perform a fluorescence observation with two-photon excitation in the near-infrared region by removing the harmonic-generating unit from the optical path, and it is possible to perform a fluorescence observation with two-photon excitation in the visible region with second harmonic waves by inserting the harmonic-generating unit to put the harmonic generating unit on the optical path.

EMBODIMENTS

Embodiments of the present invention are explained using the drawings, below.

Embodiment 1

Figure 8:
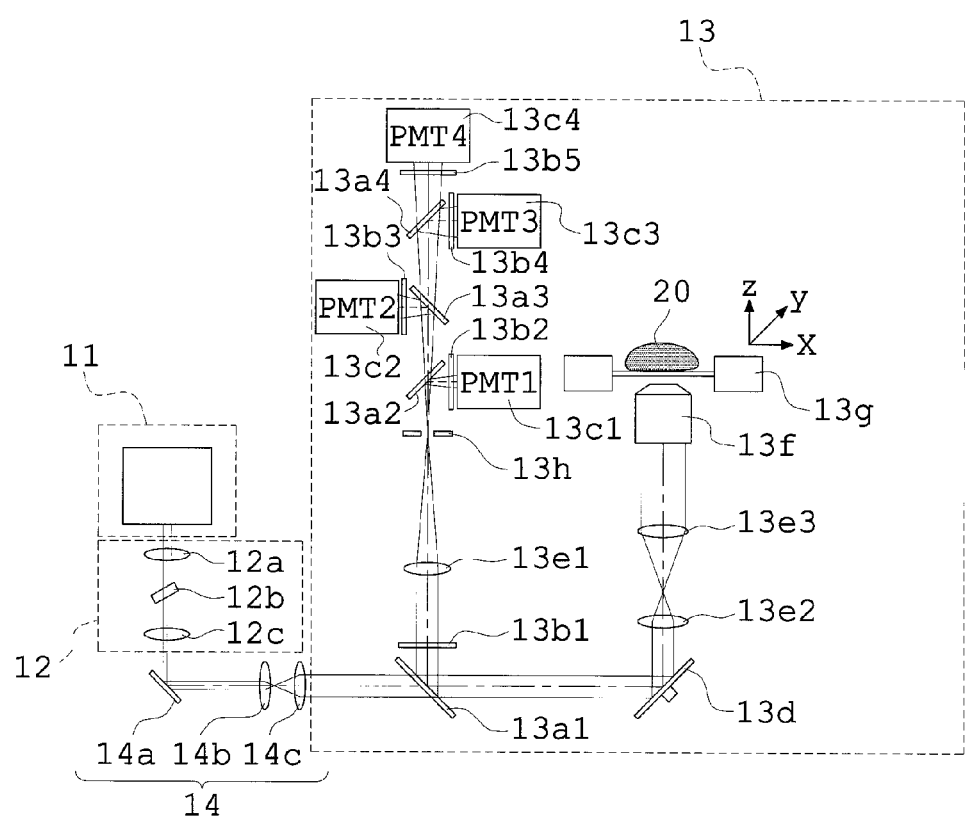
FIG. 8 is an explanatory view schematically showing the whole structure of a fluorescence observation apparatus used for a fluorescence observation method according to an embodiment 1 of the present invention.
Figure 9:
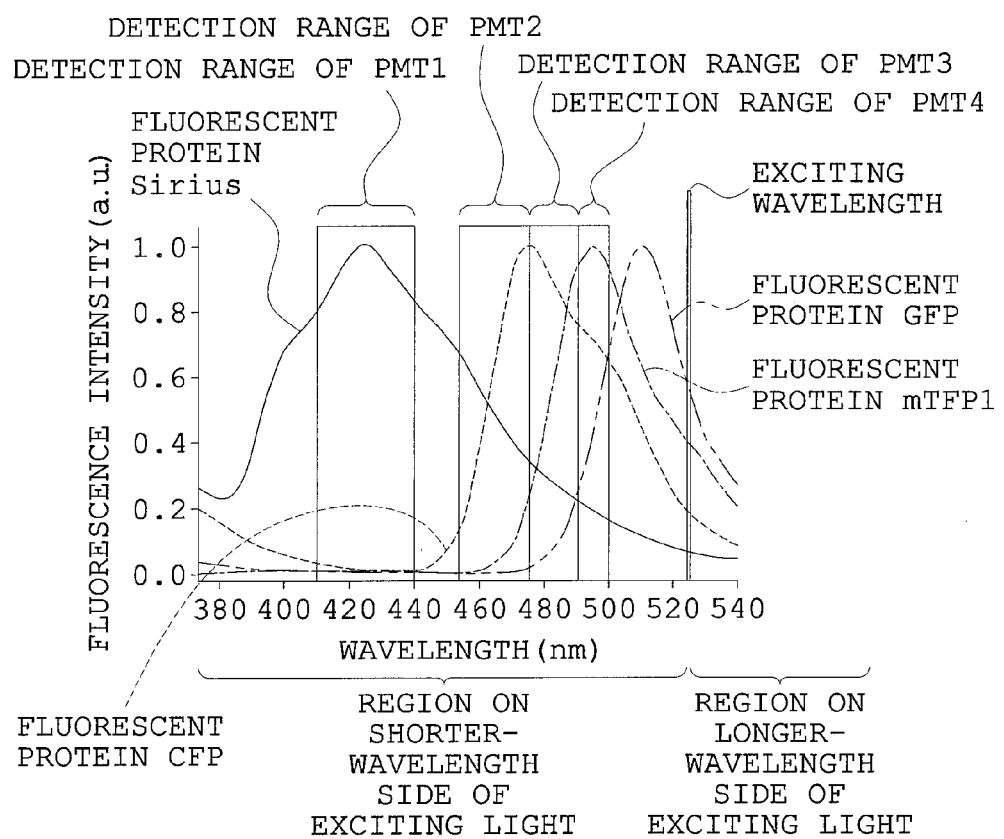
FIG. 9 is a graph showing the relation between a range of the exciting wavelengths, a range of the wavelengths of fluorescence emitted by each of fluorescent proteins, and a range of the wavelengths of fluorescence detected by each detector, in the fluorescence observation method of the embodiment 1 with the fluorescence observation apparatus.
Figure 10A:
FIGS. 10A to 10D are photographs showing fluorescent images of a HeLa cell in which four fluorescent proteins are expressed with the fluorescence observation method of the embodiment 1.
Figure 10B:
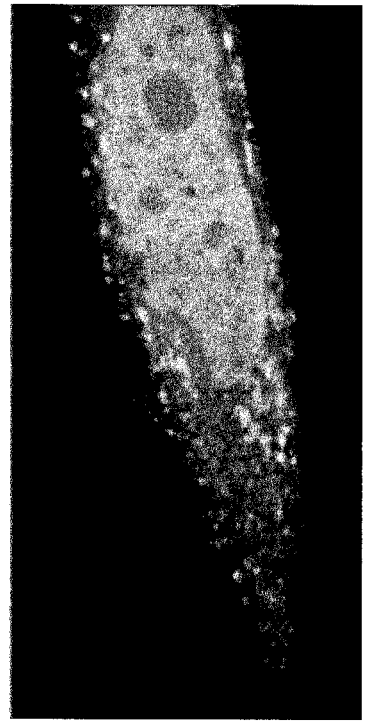
Figure 10C:
Figure 10D:
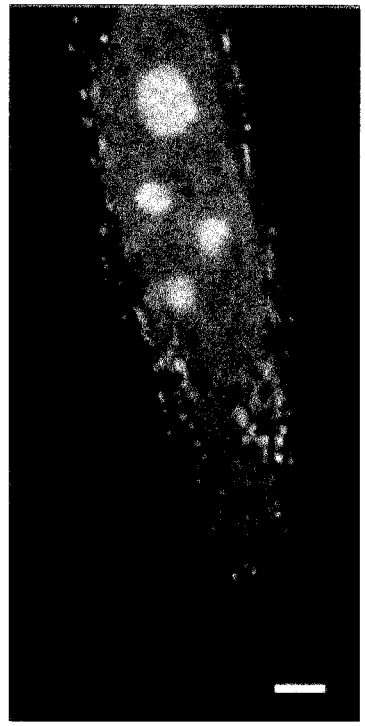

FIG. 8 is an explanatory view schematically showing the whole structure of a fluorescence observation apparatus used for a fluorescence observation method according to an embodiment 1 of the present invention. FIG. 9 is a graph showing the relation between a range of exciting wavelengths, a range of the wavelengths of fluorescence emitted by each of fluorescent proteins, and a range of the wavelengths of fluorescence detected by each detector, in the fluorescence observation method of the embodiment 1 with the fluorescence observation apparatus.

As shown in FIG. 8, a fluorescence observation apparatus in the present embodiment is provided with a light source unit 11, a second-harmonic generating unit 12, and a unit 13 for specimen observation.

The light source unit 11 is composed of a ultrashort-pulsed laser like mode-locked laser, variable wavelength laser, OPO or the like.

The second-harmonic generating unit 12 includes a lens 12a, a SHG crystal 12b like BBO crystal, and lens 12c. The SHG crystal 12b generates second harmonic waves having a wavelength of 525 nm as a wavelength of 700 nm or shorter in the visible region, with pulse laser emitted from the light source unit 11.

Besides, the fluorescence observation apparatus in the present embodiment includes a mirror 14a and lenses 14b and 14c which are optical members 14 for connecting the second-harmonic generating unit 12 and the unit 13 for specimen observation.

The unit 13 for specimen observation is composed of a microscope including: a dichroic mirrors 13a1 to 13a4; band-pass filters 13b1 to 13b5; detectors 13c1 to 13c4; a mirror 13d for two-dimensional scanning; lenses 13e1 to 13e3; an objective lens 13f; a stage 13g for three-dimensional scanning; and so on. And, the unit for specimen observation is formed to be capable of detecting plural types of fluorescence in a spectrally-selective manner with the plurality of the detectors 13c1 to 13c4 and the dichroic mirrors 13a1 to 13a4. Besides, in the drawing, the numeral reference 13h denotes a pinhole, and the numeral reference 20 denotes a specimen like a biomolecule which is labeled with a fluorescent molecule.

The specimen 20 is labeled with four kinds of fluorescent proteins (Sirius, mseCFP, mTFP1, and EGFP) as a fluorescent molecule.

The dichroic mirror 13a1 has the optical properties of transmitting light generated by the second-harmonic generating unit 12 and having a wavelength of 525 nm and of reflecting light having the other wavelengths.

The band-pass filter 13b1 has the optical properties of blocking light having wavelengths longer than the exciting light wavelength of 525 nm of plural kind of the wavelengths of fluorescence generated by plural kinds of fluorescent molecules with which the specimen 20 is labeled and of transmitting light in the other wavelength bands.

The dichroic mirror 13a2 has the optical properties of reflecting light in the wavelength band of 410 nm to 440 nm and of transmitting light in the other wavelength bands.

The band-pass filter 13b2 has the optical properties of transmitting light in the wavelength band of 410 nm to 440 nm and of blocking light in the other wavelength bands.

The dichroic mirror 13a3 has the optical properties of reflecting light in the wavelength band of 455 nm to 475 nm and of transmitting light in the other wavelength bands.

The band-pass filter 13b3 has the optical properties of transmitting light in the wavelength band of 455 nm to 475 nm and of blocking light in the other wavelength bands.

The dichroic mirror 13a4 has the optical properties of reflecting light in the wavelength band of 475 nm to 490 nm and of transmitting light in the other wavelength bands.

The band-pass filter 13b4 has the optical properties of transmitting light in the wavelength band of 475 nm to 490 nm and of blocking light in the other wavelength bands.

The band-pass filter 13b5 has the optical properties of transmitting light in the wavelength band of 490 nm to 500 nm and of blocking light in the other wavelength bands.

The detectors 13c1 to 13c4 are composed of photomultiplier tubes (PMT) respectively.

Besides, the fluorescence observation apparatus in the embodiment 1 is formed to detect fluorescence emitted by each fluorescent protein in a spectrally-selective manner through the plurality of the detectors and the dichroic mirrors (and, in addition, the band-pass filters). However, the apparatus of the present invention may be formed in such a way that these components are replaced with a multi-channel detector so that spectra are detected as optical spectra in a lump.

The mirror 13d for two-dimensional scanning is composed of a galvanometer mirror that performs scan in two-dimensional directions.

The stage 13g for three-dimensional scanning is formed to be capable of moving in three-dimensional directions with the specimen 20 put on the stage 13g.

A procedure for observing fluorescence emitted from fluorescent molecules with the fluorescence observation apparatus in the embodiment 1 having such a structure is explained.

A pulse laser beam having a predetermined wavelength is emitted at a high density using the ultrashort-pulsed laser provided for the light source unit 11. Next, the SHG crystal 12b which is provided for the second-harmonic generating unit 12 makes an oscillation to emit light having a wavelength of 525 nm as second harmonic waves using the light emitted by the light source unit 11.

Light emitted at a high density through the light source unit 11 and the second-harmonic generating unit 12 and having a wavelength of 525 nm enters the dichroic mirror 13a1 of the unit 13 for specimen observation via the optical members 14.

The dichroic mirror 13a1 transmits the light having a wavelength of 525 nm and incident on the mirror 13a1. The light transmitted by the dichroic mirror 13a1 is reflected by the mirror 13 for two-dimensional scanning, passes through the lens 13e2, the lens 13e3, and the objective lens 13f, and then is collected on a predetermined focal position in the specimen 20. Each fluorescent molecule with which the specimen 20 is labeled is excited through multi-photon excitation at each predetermined probability at the predetermined focal position in the specimen 20 by radiating to the specimen the light having a wavelength of 525 nm at a high density. The use of multi-photon absorption fluorescence makes it possible to make fluorescence in which light having a wavelength longer than wavelengths in the deep ultraviolet region is used as exciting light and the absorption property of each fluorescent molecule in the deep ultraviolet region is utilized. Besides, each of the fluorescent molecules has a property of having an absorption spectrum characterized in that: the absorption spectrum is located in the deep ultraviolet region and in the visible region; and the part of the absorption spectrum in the visible region overlaps with the wavelength of the exciting light. As a result, fluorescence having a wavelength longer than the wavelength of the exciting light also is emitted by each fluorescent molecule through one-photon excitation. Accordingly, fluorescence emitted from the fluorescent molecules include not only fluorescence deriving from two-photon excitation but also fluorescence deriving from one-photon excitation, and the fluorescence deriving from one-photon excitation intermingles with the fluorescence deriving from two-photon excitation.

Fluorescence emitted from each fluorescent molecule with which the specimen 20 is labeled through multi-photon excitation passes through the objective lens 13f, the lenses 13e3 and 13e2, and the mirror 13d for two-dimensional scanning and then is reflected by the duchroic mirror 13a1.

The light reflected by the dichroic mirror 13a1 enters the band-pass filter 13b1. The band-pass filter 13b1 blocks light having a wavelength longer than the exciting light wavelength of 525 nm and transmits light in the other wavelength bands. As a result, fluorescence generated by one-photon excitation is removed.

Light transmitted by the band-pass filter 13b1 passes through the lens 13e1 and the pinhole 13h and then enters the dichroic mirror 13a2. The dichroic mirror 13a2 reflects light in the wavelength band of 410 nm to 440 nm and transmits light in the other wavelength bands. Light reflected by the dichroic mirror 13a2 enters the band-pass filter 13b2. The band-pass filter 13b2 transmits light in the wavelength band of 410 nm to 440 nm of light incident on the band-pass filter 13b2 and blocks light in the other wavelength bands. Light in the wavelength band of 410 nm to 440 nm which is transmitted by the band-pass filter 13b2 is detected by the detector 13c1. As a result, fluorescence generated by multi-photon excitation with the absorption by the fluorescent protein, Sirius, in the deep ultraviolet region is mainly detected.

Light transmitted by the dichroic mirror 13a2 enters the dichroic mirror 13a3. The dichroic mirror 13a3 reflects light in the wavelength band of 455 nm to 475 nm of light incident on the dichroic mirror 13a3 and transmits light in the other wavelength bands. Light reflected by the dichroic mirror 13a3 enters the band-pass filter 13b3. The band-pass filter 13b3 transmits light in the wavelength band of 455 nm to 475 nm of light incident on the band-pass filter 13b3 and blocks light in the other wavelength bands. Light in the wavelength band of 455 nm to 475 nm which is transmitted by the band-pass filter 13b3 is detected by the detector 13c2. As a result, fluorescence generated by multi-photon excitation with the absorption by the fluorescent protein, CFP, in the deep ultraviolet region is mainly detected.

Light transmitted by the dichroic mirror 13a3 enters the dichroic mirror 13a4. The dichroic mirror 13a4 reflects light in the wavelength band of 475 nm to 490 nm of light incident on the dichroic mirror 13a4 and transmits light in the other wavelength bands. Light reflected by the dichroic mirror 13a4 enters the band-pass filter 13b4. The band-pass filter 13b4 transmits light in the wavelength band of 475 nm to 490 nm of light incident on the band-pass filter 13b4 and blocks light in the other wavelength bands. Light in the wavelength band of 475 nm to 490 nm which is transmitted by the band-pass filter 13b4 is detected by the detector 13c3. As a result, fluorescence generated by multi-photon excitation with the absorption by the fluorescent protein, mTFP1, in the deep ultraviolet region is mainly detected.

Light transmitted by the dichroic mirror 13b4 enters the band-pass filter 13b5. The band-pass filter 13b5 transmits light in the wavelength band of 490 nm to 500 nm of light incident on the band-pass filter 13b5 and blocks light in the other wavelength bands. Light in the wavelength band of 490 nm to 500 nm which is transmitted by the band-pass filter 13b5 is detected by the detector 13c4. As a result, fluorescence generated by multi-photon excitation with the absorption by the fluorescent protein, GFP, in the deep ultraviolet region is mainly detected.

Besides, the fluorescence detected by each of the detectors are outputted and displayed as a fluorescent image on a display device which is not shown in the drawings, through a publically-known signal-processing means or a publically-known imaging means which is not shown in the drawing.

FIGS. 10A to 10D are photographs showing fluorescent images of a HeLa cell in which four fluorescent proteins are expressed with the fluorescence observation method of the embodiment 1, and the fluorescent images shown in FIGS. 10A to 10D respectively are obtained by imaging fluorescent signals detected by the detectors 13c1 to 13c4 respectively. The four fluorescent proteins are expressed in the following organelles respectively. The wavelength of the exciting light used for imaging is 525 nm Besides, the scale bars in the drawing are 5 μm in length.

Sirius: mitochondria
mseCFP: histone H2B
mTFP1: Golgi apparatus
EGFP: fibrillarin FIGS. 11A and 11B are views showing photographs of an image which is obtained in such a way that fluorescence signals detected by the detectors 13c1 to 13c4 are processed with a fluorescence-wavelength separating (UNMIXING) method for fluorescent images of the HeLa cell in which the four fluorescent proteins are expressed with the fluorescence observation method of the embodiment 1 and then the fluorescent images are overlapped: FIG. 11A is a fluorescent image of the cell on a X-Y plane; and FIG. 11B is a fluorescent image of the cell on a X-Z plane.

Besides, the scale bars in the drawing are 5 μm in length.

Besides, although fluorescent proteins are used as a fluorescent molecule in the embodiment 1, the fluorescence observation method of the present invention are also applicable to fluorescent molecules except fluorescent proteins (for example, fluorescent dyes made up of chemical synthetic substances).

Figure 12:
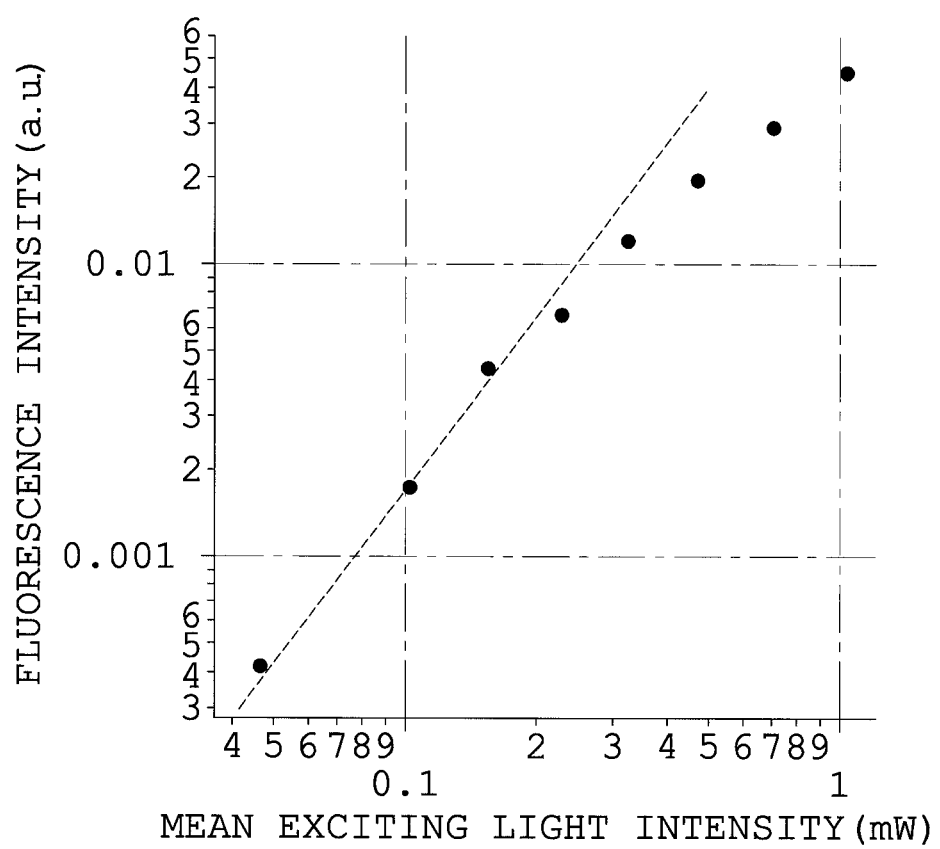
FIG. 12 is graph showing the relation between the fluorescence intensity and the exciting light intensity of a fluorescent dye, ATTO488.
Figure 13:
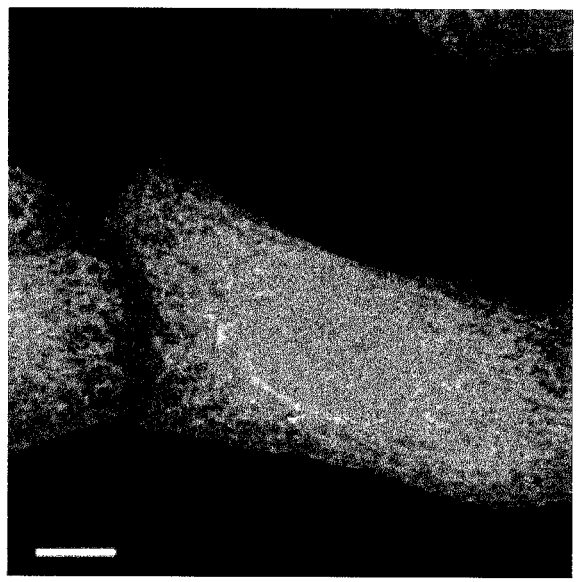
FIG. 13 is a photograph showing a fluorescent image of a cytochrome c excited with pulsed light of 520 nm, in a HeLa cell dyed with ATTO488.

FIG. 12 is graph showing the relation between the fluorescence intensity and the exciting light intensity of a fluorescent dye, ATTO488. Fluorescence is generated through excitation with a pulse laser beam having a wavelength of 560 nm and a pulse width of 200 femtosecond. FIG. 13 is a photograph showing a fluorescent image of a cytochrome c in the HeLa cell dyed with ATTO488 that is excited by pulse light of 520 nm. The scale bar in FIG. 13 is 5 μm in length.

As shown in FIG. 12, when a pulse laser beam having a wavelength of 560 nm and a pulse width of 200 femtosecond is radiated to the ATTO488, the fluorescence intensity is proportional to the square of the exciting light intensity. For this reason, detected fluorescence emitted from the ATTO488 also is generated by two-photon excitation, and it is clear that two-photon excitation in the visible wavelength region according to the fluorescence observation method of the present invention is also applicable to chemical synthetic substances except fluorescent proteins.

In addition, it is already verified that the present invention is also applicable to a fluorescent dye, Mitotracker Green.

Besides, a pre-chirper which adjusts the pulse width of a ultrashort-pulsed beam by generating negative dispersion in the group velocity of the ultrashort-pulsed beam may be provided for the second-harmonic generating unit 12 (the pre-chirper is omitted in the drawings). Such a manner makes it possible to control the pulse width on a specimen surface and makes it possible to approximately make a Fourier-limited pulse on the specimen surface. As a result, the efficiency of two-photon excitation increases, and the fluorescence intensity of generated fluorescence becomes large.

Also, the pinhole 13h is placed on the optical path in the embodiment 1. However, needless to say, a fluorescence observation apparatus according to the present invention may have a structure in which the pinhole is not provided for the fluorescence observation apparatus.

Also, although the lens 13e1 and the pinhole 13h are placed in front of the dichroic mirrors 13a2, 13a3, and 13a4 and the band-pass filter 13b5 in the embodiment 1, the pair of the lens 13e1 and the pinhole 13h may be placed in the rear of each of the dichroic mirrors 13a2, 13a3, and 13a4 and the band-pass filter 13b5. Such a manner makes it possible to optimize the position of and the diameter of the pinhole 13h in accordance with the wavelength of fluorescence incident on each of the detectors 13c1 to 13c4, and it is possible to detect fluorescence efficiently.

Also, in the case where there exist fluorescence generated by one-photon excitation and fluorescence generated by two-photon excitation simultaneously, the intensity of exciting light may be modulated with a single frequency using an acousto-optic system or the like (which is omitted in the drawings) and then the intensity of fluorescence detected by the detectors 13c1 to 13c4 may be demodulated with a frequency that is two times as large as the modulated frequency with a lock-in amplifier or the like (which is omitted in the drawings) so that fluorescence components generated by one-photon excitation and fluorescence components generated by two-photon excitation are separated from each other and only fluorescence components by two-photon excitation are extracted. Such a manner makes it possible to improve resolving power in the case where it is difficult to split fluorescence with filters.

Also, for example, the wavelength width of exciting light wavelength may be shaped using an edge filter or the like (which is omitted in the drawings) so that the wavelength width of the exciting light wavelength becomes 7 to 10 nm. Such a manner makes it easy to separate fluorescence and exciting light from each other, and, also, it is possible to detect fluorescence emission more efficiently. However, this wavelength width is not limited to these values, and the wavelength width of exciting light may be changed to become optimum in accordance with fluorescent proteins, exciting light wavelengths, or the like which is used for the fluorescence observation method of the present invention.

A fluorescence observation method and a fluorescence observation apparatus according to the present invention are useful for every field that requires simultaneous observation of fluorescence emitted from plural kinds of fluorescent molecules respectively.

What is claimed is:

1. A fluorescence detection method for detecting plural types of fluorescence emitted from two or more kinds of fluorescent molecules, comprising:
   subjecting each of the two or more kinds of fluorescent molecules to multi-photon excitation by exciting light having an exciting wavelength equal to or shorter than 525 nm in a visible region so that each of the two or more kinds of fluorescent molecules is raised to a second excited level higher than a first excited level and then returns to a ground level to generate fluorescence upon making use of an absorption wavelength band in a deep ultraviolet region of each of the two or more kinds of fluorescent molecules; and
   simultaneously detecting plural types of fluorescence generated on a shorter-wavelength side or on both of the shorter-wavelength side and a longer-wavelength side of the exciting wavelength of the exciting light.

2. The fluorescence detection method according to claim 1, wherein each of the two or more kinds of fluorescent molecules used for a fluorescence detection target has absorption wavelength bands in the deep ultraviolet region and in the visible region.

3. The fluorescence detection method according to claim 1, wherein the exciting light is an ultrashort-pulsed laser beam.

4. The fluorescence detection method according to claim 1, wherein only fluorescence generated on the shorter-wavelength side of the exciting wavelength is detected via a short-pass filter.

5. The fluorescence detection method according to claim 1, wherein fluorescence having a wavelength of 400 nm or longer generated on the shorter wavelength side of the exciting wavelength is detected.

6. The fluorescence detection method according to claim 1, wherein the plural types of fluorescence generated via the multi-photon excitation are detected in a spectrally-selective manner.

7. The fluorescence detection method according to claim 1, wherein the plural types of fluorescence generated via the multi-photon excitation are detected through confocal detection.

8. The fluorescence detection method according to claim 1, wherein fluorescence deriving from one photon and fluorescence deriving from two photons, which are generated via the multi-photon excitation, are simultaneously detected.

9. A fluorescence observation apparatus comprising:
   a light source that emits light having a predetermined wavelength;
   a second-harmonic generating element that generates second harmonic waves having a wavelength of 525 nm or shorter in a visible region, using the light from the light source; and
   a microscope configured to subject each of two or more kinds of fluorescent molecules to multi-photon excitation by the second harmonic waves, as exciting light, generated by the second-harmonic generating element so that each of the two or more kinds of fluorescent molecules is raised to a second excited level higher than a first excited level and then returns to a ground level to generate fluorescence, the microscope being further configured to make plural types of fluorescence generated on a shorter-wavelength side or on both of the shorter-wavelength side and a longer-wavelength side of the wavelength of the exciting light simultaneously observable.

10. The fluorescence observation apparatus according to claim 9, wherein the light source unit and the second-harmonic generating element are integrally formed into an exciting light generating unit, to provide the exciting light to the microscope so that the plural kinds of the fluorescent molecules are subjected to multi-photon excitation.

11. The fluorescence observation apparatus according to claim 9, wherein the second-harmonic generating element is configured to be insertable in and removable from a path of light from the light source.

* * * * *